United States Patent
Küster et al.

(10) Patent No.: US 8,991,244 B2
(45) Date of Patent: Mar. 31, 2015

(54) TESTING DEVICE FOR CHECKING THE QUALITY OF A PAINT OR LACQUER LAYER

(75) Inventors: Rafael Küster, Esslingen (DE); Olaf Eistert, Birenbach (DE); Tobias Burk, Tuebingen (DE); Roland Emmerich, Beilstein (DE)

(73) Assignee: Robert Bosch GmbH, Stuttgart (DE)

( * ) Notice: Subject to any disclaimer, the term of this patent is extended or adjusted under 35 U.S.C. 154(b) by 461 days.

(21) Appl. No.: 13/134,191

(22) Filed: May 31, 2011

(65) Prior Publication Data

US 2012/0103080 A1 May 3, 2012

(30) Foreign Application Priority Data

Jun. 16, 2010 (DE) .................. 10 2010 030 159

(51) Int. Cl.
*G01B 21/08* (2006.01)
*G01N 33/32* (2006.01)
*G01N 3/56* (2006.01)

(52) U.S. Cl.
CPC . *G01N 33/32* (2013.01); *G01N 3/56* (2013.01)
USPC .............................................. 73/150 R; 73/7

(58) Field of Classification Search
CPC ........... G01N 3/56; G01N 3/46; G01N 19/02; G01N 2203/0286; G01N 19/04; G01N 33/32
USPC ........ 73/7, 9, 10, 150 R, 150 A, 54.01, 54.02, 73/54.23
See application file for complete search history.

(56) References Cited

U.S. PATENT DOCUMENTS

| | | | |
|---|---|---|---|
| 2,287,148 A | 6/1942 | Taber | |
| 2,316,518 A | 4/1943 | Klenke, Jr. | |
| 2,966,790 A | 1/1961 | Walker | |
| 3,040,559 A | 6/1962 | Adams | |
| 3,100,981 A | 8/1963 | Engle et al. | |
| 3,973,432 A | 8/1976 | Toulc'Hoat et al. | |
| 3,974,678 A | 8/1976 | Rooney et al. | |
| 5,985,987 A | 11/1999 | Adolfsson et al. | |
| 2004/0051543 A1* | 3/2004 | Ryder et al. | 324/754 |
| 2009/0078035 A1* | 3/2009 | Mecca et al. | 73/150 R |
| 2009/0320575 A1* | 12/2009 | Hangen | 73/105 |
| 2011/0199098 A1* | 8/2011 | Bense et al. | 324/637 |

FOREIGN PATENT DOCUMENTS

DE 3331172 A1 * 3/1985
DE 197 02 267 7/1998

* cited by examiner

*Primary Examiner* — Daniel S Larkin
*Assistant Examiner* — Jamar Ray
(74) *Attorney, Agent, or Firm* — Kenyon & Kenyon LLP (57) ABSTRACT

A testing device for checking the quality of a paint or lacquer layer includes at least one friction element moving device. To prevent an impression on a test region, the friction element moving device is configured to (i) initially move at least one friction element in frictional contact along a defined path, e.g., a circular path, over a test region of a paint or lacquer layer, and (ii) subsequently eliminate the frictional contact between the friction element and the test region during the movement of the friction element.

18 Claims, 5 Drawing Sheets

TESTING DEVICE FOR CHECKING THE QUALITY OF A PAINT OR LACQUER LAYER

BACKGROUND OF THE INVENTION

1. Field of the Invention

The present invention relates to a testing device for checking the quality of a paint or lacquer layer, and a corresponding method.

2. Description of the Related Art

In latex paints and lacquers, solvents or water as well as other volatile substances escape from the still wet layer after application. Since the composition of the lacquer is therefore constantly changing during the drying phase, flocculation (reagglomeration) of the pigments contained therein may occur. In addition, demixing of pigments having different densities, for example titanium dioxide and copper phthalocyanin, may occur. In the worst-case scenario, hexagonal cells, so-called Bénard cells, are formed which are caused by flow within the lacquer layer.

Shear forces are introduced into the system as the result of rubbing during drying. It is thus possible to disaggregate (deagglomerate) the agglomerates, i.e., eliminate the demixing. The rubbed surface may thus have an appearance which is significantly different from, usually more intensely colored than, the unrubbed surface.

The difference between a rubbed surface of a paint or lacquer layer and an unrubbed reference surface of the paint or lacquer layer is referred to as the "rubout effect." The rubout effect is stronger the more intensely colored/weakly colored is the appearance of the rubbed surface in comparison to the unrubbed surface. If the rubbed surface has a more intensely colored appearance than the unrubbed surface, this is referred to as a positive rubout effect, and if the rubbed surface has a more weakly colored appearance, this is referred to as a negative rubout effect. In the ideal case, no differences in color intensity or hue are apparent.

The rubout test is conventionally carried out manually, in that the person conducting the test rubs a bare finger, a gloved finger, or a brush over the test region to be checked. Depending on the paint or lacquer system, rubbing with the bare finger may have adverse health effects over the long term. On the other hand, the viscosity limit is practically imperceptible using laboratory gloves. When a brush is used for testing, the brush must be laboriously cleaned, which is one reason, among others, that this method is seldom used.

In addition, defining a test period is problematic. For example, a rubout test using the bare finger may be carried out until the lacquer "pulls up," i.e., until a specific limiting viscosity of the lacquer which is perceived by the tester is reached. However, identifying an end point independently of the tester is extremely difficult. On the other hand, setting a defined test period, for example in order to standardize the overall energy input during the testing, does not take into account differences between testers or different drying times due to system-related factors, since breakup of the flocculate is effective only when it is also stabilized by the advanced-stage drying.

Lastly, the conditions under which a rubout test is to be carried out have not been normatively defined. In most cases, the result of the rubout test is highly dependent on the tester and his physical and mental state on a given day. In addition, the results from different laboratories are rarely comparable due to differing procedures. Approaches according to which checking of the quality of a paint or lacquer layer may be automated are described in U.S. Pat. No. 2,316,518 A1, U.S. Pat. No. 2,287,148 A, U.S. Pat. No. 3,040,559 A, and U.S. Pat. No. 3,974,678.

BRIEF SUMMARY OF THE INVENTION

The present invention provides a testing device for checking, in particular automatically, the quality of a (latex) paint or lacquer layer, and which includes at least one friction element moving device. According to the present invention, the friction element moving device may be designed to move at least one friction element, in particular automatically, in frictional contact along a defined path over a test region of a paint or lacquer layer, and/or to eliminate, in particular automatically, the frictional contact between the friction element and the test region during the (continuing) movement of the friction element.

A friction element moving device has the advantages that the rubout test method is standardized, operator-related deviations are avoided, and the reproducibility of the test results may be increased. In addition, by using a friction element moving device, direct contact of the operator with the paint or lacquer formulation may advantageously be avoided (health protection).

Eliminating the frictional contact between the friction element and the test region during movement of the friction element has the advantage that impressions on the test region are prevented. This has the advantage, in turn, that the comparability of such test regions is increased, and errors resulting from a background which shows through (variations in layer thickness) are avoided, thus improving the quality checking.

The testing device may be a semiautomatic or fully automatic testing device for use in the laboratory or use in a facility for high-throughput research (high-throughput facility). For example, the testing device may be a semiautomatic testing device, for example for use in the laboratory, which is manually provided with friction elements and paint- or lacquer-coated substrates, for example. However, the testing device may also be a fully automatic testing device, for example for use in a facility for high-throughput research (high-throughput facility), which, for example, automatically produces the paint or lacquer, installs the substrate, coats the substrate, installs the friction element, moves the friction element, optionally cleans the friction element, and carries out the evaluation.

In particular the friction element moving device of the testing device may be designed for temperatures which are equal to or greater than the melting or liquefaction temperature range of powder lacquers. For example, the friction element moving device may be designed for use at temperatures of up to 220°. In this way, the testing device may also be used to check the quality of powder lacquers which are present in liquid form only at elevated temperatures.

The frictional contact between the friction element and the test region may be eliminated during movement of the friction element by moving the friction element, during the (continuing) movement thereof, out of the test region and/or by lifting it from the test region. Using both alternatives or also a combination of these alternatives, impressions on the test region may be prevented, which is accompanied by the previously described advantages.

Thus, in one specific embodiment, the friction element moving device is designed to move the friction element, in particular automatically, out of the test region during the (continuing) movement of the friction element.

Thus, in another specific embodiment the friction element moving device is designed to lift the friction element, in particular automatically, from the test region during the (continuing) movement of the friction element.

In another specific embodiment, the friction element moving device is designed to move the friction element in frictional contact along a defined path over a test region of an unmoved/stationary paint or lacquer layer. The testing device may be simplified as a result of the paint or lacquer layer not being moved.

In another specific embodiment, the friction element moving device is designed to move the friction element in frictional contact along a defined, at least partially curved, path over a test region. In this way the motion of a manually performed rubout test, which is usually a circular motion, may be simulated, which increases the comparability. On the other hand, when the friction element is only moved back and forth linearly, the still liquid coating material may be laterally displaced, which may result in a great decrease in the layer thickness and may allow the background to show through, thus possibly distorting the results. In addition, points on the friction element may move on circular paths having different center points, thus ensuring optimal intermixing of the demixed pigments, i.e., disaggregation of agglomerates, and allowing the measuring surface to be enlarged.

In another specific embodiment, the friction element moving device is designed in such a way that the shape of the friction element path is adjustable, in particular automatically. Individual, reproducible rubout motions may be achieved in this way. For example, the friction element moving device may be designed in such a way that the friction element path includes a first, curved path segment in the test region and a second, linear path segment outside the test region. For example, the first, curved path segment may have a spiral shape, or the shape of a singly or multiply run-through oval, in particular a circle or ellipse. The second, linear path segment may, for example, be a path segment which extends tangentially with respect to the first, curved path segment. An impression on the evaluation site may likewise be avoided in this way.

In another specific embodiment, the friction element moving device includes at least one, in particular automatic, gripper for detachably, in particular automatically, fastening a friction element. The gripper is preferably designed to automatically grip, fix, and release a friction element. The gripper may in particular be a vacuum gripper.

The friction element is preferably designed, in particular with regard to the shape, size, flexibility, hardness, and/or surface quality, in such a way that optimal disaggregation of agglomerates, i.e., elimination of demixing, is achieved. The friction element is preferably designed in such a way that the paint or lacquer layer is not laterally displaced. A covering paint or lacquer layer may thus be obtained after the frictional contact. For example, the friction element may simulate a human finger, in particular with regard to the flexibility, hardness, and/or surface quality. However, the friction element may also be a brush-shaped element or an element having a flat (planar) rubbing surface, for example a flat disk, or an element having a convex rubbing surface, for example a rounded/cambered disk, an ovaloid, a semiovaloid, an ellipsoid, a semiellipsoid, a sphere, or a hemisphere.

In another specific embodiment, the friction element is an element having a convex rubbing surface, for example a rounded/cambered disk, an ovaloid or a semiovaloid, in particular an ellipsoid, a semiellipsoid, a sphere, or a hemisphere.

In another specific embodiment the friction element is cleanable, in particular automatically cleanable, or is a disposable part. The use of disposable friction elements has the advantages that no cleaning is necessary, and rapid and operationally reliable color changes may be made.

In another specific embodiment, the friction element moving device is designed in such a way that the bearing force with which the friction element lies on the paint or lacquer layer is adjustable, in particular automatically and/or in a reproducible manner. In this way a rubout test may be carried out using different bearing forces on a paint or lacquer layer. In addition, the rubout test may thus be adapted to different paint or lacquer formulations and/or layer thicknesses.

For example, the bearing force may be adjustable using one or multiple mountable or adjustable weights and/or one or multiple springs and/or a motor and/or a cylinder. In particular when springs are used, in addition at least one vibration damper may be used in order to damp vibrations caused by the spring.

In another specific embodiment, the friction element moving device is designed in such a way that the rubout time, during which the at least one friction element is in frictional contact with the test region, is adjustable, in particular automatically and/or in a reproducible manner. The overall energy input may thus be standardized and reproduced.

The friction element moving device is preferably designed to place the friction element, in particular automatically, on the test region of the paint or lacquer layer during movement of the friction element. In this way impressions on the test region may likewise be prevented.

In another specific embodiment, the friction element moving device includes at least one force sensor for measuring a force which acts laterally on the friction element during frictional contact. For example, the friction element moving device may include at least one force sensor for each friction element for measuring a force which acts laterally on the friction element. With the aid of such force sensors, for example, the drying state of the paint or lacquer layer may be identified, and the rubout time may be adapted to the paint or lacquer layer formulation, the friction element, and/or the substrate.

In particular, the testing device may include multiple friction elements for checking the quality of a paint or lacquer layer in multiple test regions. In this way, multiple rubout tests may be carried out simultaneously under identical conditions (times, motion paths) on one or multiple substrates having the same or different friction elements, for example for comparative testing of a sample and of a reference formulation.

Thus, in one specific embodiment the friction element moving device is designed to move at least one first friction element and at least one second friction element, in each case in frictional contact along a defined path over a test region. For example, the first friction element(s) may each be moved in frictional contact along a defined path over a test region of a paint or lacquer layer, and the second friction element(s) may each be moved in frictional contact along a defined path over a test region of a reference. In particular, the friction element moving device may be designed to move multiple first friction elements, in each case in frictional contact along a defined path over a test region of a paint or lacquer layer, and/or one or multiple second friction element(s), in each case in frictional contact along a defined path over a test region of a reference, in particular a reference paint layer or reference lacquer layer.

In one embodiment, the shapes of the rubbing paths and the rubout times of the first friction elements and/or second friction elements are equal or at least essentially equal. In particular, the friction element moving device may be designed to move the first and second friction elements at the same time. In this way the quality of multiple paint or lacquer layers may be checked under identical and reproducible conditions and compared to the reference. In principle, the bearing forces of the friction elements may likewise be equal or at least essentially equal.

However, in one particular embodiment, the bearing forces of the individual friction elements may be adjusted differently. In particular, the bearing forces of the first friction elements may be adjusted differently from one another, and/or the bearing forces of the second friction elements may be adjusted differently from one another. This may be ensured, for example, in that each friction element is supported individually, and/or in that the friction element moving device includes an individual weight-based, spring-based, and/or motorized bearing force adjusting system for each friction element. This has the advantage, for example, that on the one hand the influence of the bearing force on the quality of a paint or lacquer layer or paint or lacquer formulation may be investigated. On the other hand, this has the advantage, for example, that the test conditions may be individually adapted to different paint or lacquer layers, for example having different thicknesses, or different paint or lacquer formulations, and in this way the quality of multiple different paint or lacquer layers or formulations may be checked at the same time in one work step.

Alternatively or additionally, the testing device may include two or more friction element moving devices.

In another specific embodiment, the testing device includes two or more friction element moving devices, the friction element moving devices each being designed to move at least one friction element in frictional contact along a defined path over a test region of a paint or lacquer layer, and to eliminate the frictional contact between the friction element and the test region during the (continuing) movement of the friction element. The friction element moving devices may each be designed to move only one friction element, only one first friction element and one second friction element, or one or multiple first friction element(s) and one or multiple second friction element(s), in each case in frictional contact along a defined path over a test region. For example, the friction element moving devices may each be designed to move the first friction element(s) in each case in frictional contact along a defined path over a test region of a paint or lacquer layer, and to move the second friction element(s) in each case in frictional contact along a defined path over a test region of a reference. In particular, the friction element moving devices may each be designed to move multiple first friction elements in each case in frictional contact along a defined path over a test region of a paint or lacquer layer, and/or to move one or multiple second friction elements in each case in frictional contact along a defined path over a test region of a reference, in particular a reference paint layer or reference lacquer layer.

The shapes of the rubbing paths and the rubout times of the friction elements of the individual friction element moving devices may be the same or different. In addition, the individual friction element moving devices may be designed to move their friction elements simultaneously or at different points in time. In this way the quality of multiple paint or lacquer layers may be checked under different, reproducible conditions, for example after different drying times.

In principle, the bearing forces of the friction elements of the individual friction element moving devices may likewise be the same. However, in one particular embodiment the bearing forces of the friction elements of the individual friction element moving devices may be adjusted differently. This may be ensured, for example, in that the friction element moving devices are each individually supported and/or have an individual weight-based, spring-based, and/or motorized bearing force adjusting system. In addition, the bearing forces of the individual friction elements may be adjusted differently within a friction element moving device. As previously explained, this may be ensured in that the friction elements are each individually supported and/or have an individual weight-based, spring-based, and/or motorized bearing force adjusting system.

The testing device may also include a substrate fixing device. For example, the substrate fixing device may include a base body having one or multiple recesses for accommodating substrates, in particular test cards. By inserting one substrate into each recess it may be ensured, for example, that a paint or lacquer layer applied to the substrate remains unmoved during the rubout motion of the friction element. Alternatively or additionally, the substrate fixing device may include one or multiple clamps for clamping substrates.

The testing device may also include a coating device for automatically coating substrates, for example test cards, using one or multiple paint or lacquer layer(s) which is/are the same or different. The coating device may, for example, automatically apply a paint or lacquer layer to the substrate using a blade coating, spray coating, roller coating, and/or spin coating method.

In addition, the testing device may include a paint or lacquer production unit for automatically producing/mixing paint or lacquer formulations.

In addition, the testing device may include a substrate fitting device for fitting the testing device with one or multiple substrates and for removing the coated and tested substrates. The substrate fitting device may be designed to automatically remove one or multiple substrates from a substrate supply reservoir, and to automatically release same into a substrate collection reservoir after the test has been carried out.

In addition, the testing device may include a friction element supply reservoir for supplying friction elements for carrying out the test, and/or a friction element collection reservoir for collecting friction elements after the test has been carried out. The gripper(s) may be designed to automatically grip one friction element from the friction element supply reservoir in each case, and to release same into the friction element collection reservoir after the test has been carried out. The friction element collection reservoir may be designed in such a way that the friction elements therein are automatically cleaned and subsequently returned to the friction element supply reservoir. However, the testing device may also include a friction element cleaning device which is designed to automatically remove friction elements from the friction element collection reservoir, automatically clean them, and automatically return them to the friction element supply reservoir. However, it is also possible to provide the friction element supply reservoir with disposable friction elements, and to dispose of the used disposable friction elements which are collected in the friction element collection reservoir. Expenditure of effort by personnel for cleaning may be minimized in this way.

In addition, the testing device may include an evaluation device for evaluating the influence of the frictional contact on the test region(s), for example with the aid of color measurement and/or gloss measurement.

A further subject matter of the present invention is a test method for checking, in particular for automatically checking, the quality of a (latex) paint or lacquer layer, in particular using a testing device according to the present invention.

According to the present invention, in this method at least one friction element is automatically moved in frictional contact along a defined path over a test region of a paint or lacquer layer, and/or the frictional contact between the friction element and the test region is automatically eliminated during the (continuing) movement of the friction element.

With regard to the advantages and additional features of the test method, explicit reference is hereby made to the advantages and features explained in conjunction with the testing device.

In particular, the friction element may be automatically moved in frictional contact along a defined, at least partially curved, path over the test region.

Alternatively or additionally, within the scope of the test method the friction element may be automatically moved in frictional contact along a defined path over a test region of an unmoved/stationary paint or lacquer layer.

Within the scope of the test method, the shape of the friction element path may be automatically adjusted. For example, the friction element path may include a first, curved path segment in the test region and a second, linear path segment outside the test region. For example, the first, curved path segment may have a spiral shape, or the shape of a singly or multiply run-through oval, in particular a circle or ellipse. The second, linear path segment may, for example, be a path segment which extends tangentially with respect to the first, curved path segment.

In another specific embodiment, the frictional contact between the friction element and the test region is eliminated by automatically moving the friction element out of the test region and/or by lifting it from the test region during the (continuing) movement of the friction element. For example, after a defined rubout time ($t_R$) has elapsed or a defined lateral force ($F_R$, drying of the lacquer) on the friction element has been exceeded, the friction element may be moved, for example tangentially, from the test position/rubbing position and lifted off outside the rubbing position.

In principle, the movement of the friction element may be started during or after it is brought into contact with the test region. However, the movement of the friction element may also be started before it is brought into contact with the test region or is placed on the test region, the moved friction element being brought into contact with the test region. This has the advantage that impressions in the test region may be avoided.

The moved friction element may be automatically placed on the test region. In particular, the friction element may be placed on the test region with a defined bearing force. The defined bearing force ($F_A$) may be automatically adjusted.

In another specific embodiment, the paint or lacquer layer is automatically applied to a substrate, a test card, for example. This may be carried out automatically on the substrate using a blade coating, spray coating, roller coating, and/or spin coating method, for example. For this purpose, the paint or lacquer formulation for the paint or lacquer layer may likewise be automatically produced or mixed.

In another specific embodiment, the friction element is automatically brought into contact with the test region after a defined waiting time/drying time ($t_T$) after the paint or lacquer layer has been applied. The waiting time/drying time ($t_T$) may likewise be automatically adjusted.

In another specific embodiment, the friction element is moved in frictional contact over the test region for a defined rubout time ($t_R$). The rubout time ($t_R$) may likewise be automatically adjusted. The test region may be automatically evaluated after the defined rubout time ($t_R$) has elapsed.

After the frictional contact has been eliminated, the friction element may be cleaned, in particular automatically, and/or replaced with a cleaned friction element or disposable friction element, for example.

In another specific embodiment, the force ($F_R$) which acts laterally on the friction element during frictional contact is measured and used as a measure of the state, in particular the drying state, of the paint or lacquer layer, and/or as a measure of the elimination/termination of the frictional contact, in particular at a defined point. The quality testing (rubout test) or the rubout time may thus be automatically adapted to different paint or lacquer formulations, friction elements, and substrates.

The friction element may be automatically gripped, for example by an automatic gripper, in particular an automatic vacuum gripper, at the start of the test, automatically fixed/held during the test, and automatically released when the test has been concluded.

Within the scope of the test method, in particular the quality of multiple paint or lacquer layers may be checked via a rubout motion of multiple friction elements in multiple test regions and compared to references. For this purpose, for example, at least one first friction element and at least one second friction element in each case may be moved in frictional contact along a defined path over a test region. For example, the first friction element(s) in each case may be moved in frictional contact along a defined path over a test region of a paint or lacquer layer, and the second friction element(s) in each case may be moved in frictional contact along a defined path over a test region of a reference, in particular a reference paint layer or reference lacquer layer. The shapes of the rubbing paths and the rubout times of the friction elements may be the same or different. In addition, the friction elements may be moved simultaneously or at different points in time.

In principle, the bearing forces of the friction elements may be the same. However, in one particular embodiment the bearing forces of the individual friction elements may be adjusted differently.

The test method may be carried out semiautomatically or fully automatically, in the laboratory or in a facility for high-throughput research (high-throughput facility). For example, the test method may be carried out semiautomatically, for example in the laboratory, the friction elements and color- or lacquer-coated substrates being installed manually. However, the test method may also be carried out fully automatically, for example in a facility for high-throughput research (high-throughput facility), the paint or lacquer production, the substrate installation, the substrate coating, the friction element installation, the movement of the friction element, optionally the friction element cleaning, and the evaluation being carried out automatically. In addition, within the scope of the test method the influence of the frictional contact on the test region(s) may in particular be automatically evaluated, for example using an evaluation device with the aid of color measurement and/or gloss measurement, for example.

DETAILED DESCRIPTION OF THE INVENTION

Figure 1A:
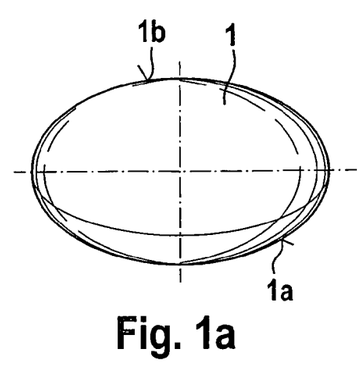
FIG. 1a shows a schematic perspective view of one specific embodiment of an ovaloid friction element.

FIG. 1a shows a schematic perspective view of one specific embodiment of an ovaloid friction element 1. Such a friction element 1 may also be referred to as a friction element in the form of a disk that is cambered on both sides. FIG. 1a shows that friction element 1 has a convex rubbing surface 1a. FIG. 1a further shows that surface 1b of friction element 1, which is situated opposite from rubbing surface 1a, also has a convex design. This is likewise illustrated by the schematic cross section of this specific embodiment (perpendicular to the rubbing planes) shown in FIG. 1b. Such a friction element 1 may be gripped, fixed, and released by a vacuum gripper, for example.

Figure 1B:
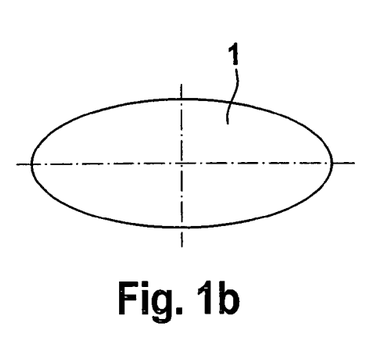
FIG. 1b shows a schematic cross section of the specific embodiment of a friction element shown in FIG. 1a, perpendicular to the rubbing plane.
Figure 1C:
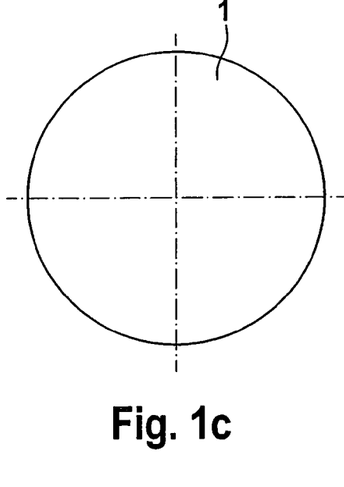
FIG. 1c shows one alternative of the specific embodiment, shown in FIGS. 1a and 1b, of a friction element having a circular cross section parallel to the rubbing plane.
Figure 1D:
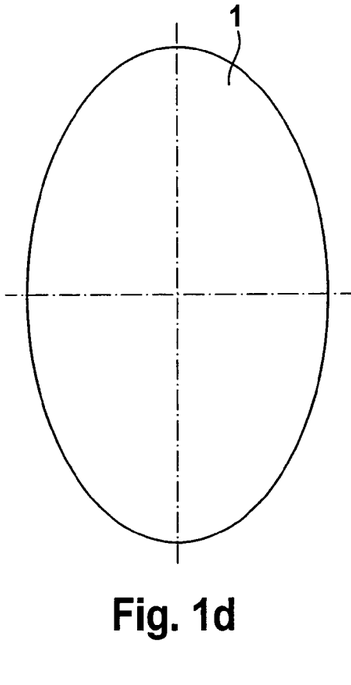
FIG. 1d shows another alternative of the specific embodiment, shown in FIGS. 1a and 1b, of a friction element having an oval cross section parallel to the rubbing plane.

FIGS. 1c and 1d illustrate that ovaloid friction element 1 from FIGS. 1a and 1b may have different cross-sectional designs parallel to the rubbing plane. FIG. 1c shows one alternative having a circular design parallel to the rubbing plane, and FIG. 1d shows one alternative having an oval design parallel to the rubbing plane.

Figure 2:
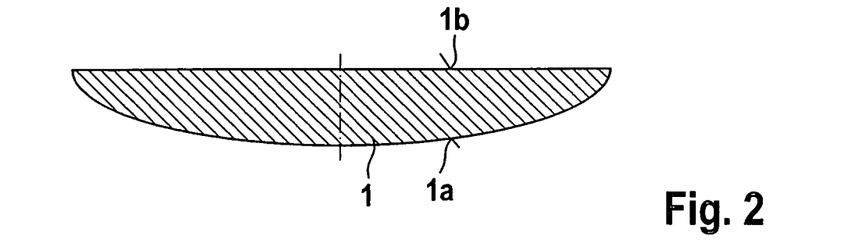
FIG. 2 shows a schematic cross section of one specific embodiment of a friction element in the form of a semiovaloid or a disk which is cambered on one side.

FIG. 2 shows a schematic cross section of one specific embodiment of a friction element 1 in the form of a semiovaloid, i.e., a disk that is cambered on one side. FIG. 2 shows that this friction element 1 also has a convex rubbing surface 1a. In contrast to friction elements 1 shown in FIGS. 1a through 1d, however, surface 1b of friction element 1 which is situated opposite from rubbing surface 1a is flat. Such a friction element 1 may likewise be gripped, fixed, and released by a vacuum gripper. Such a friction element 1 may optionally have a gripping section (not illustrated) on surface 1b which is situated opposite from rubbing surface 1a and which may be gripped by a mechanical gripper.

Figure 3:
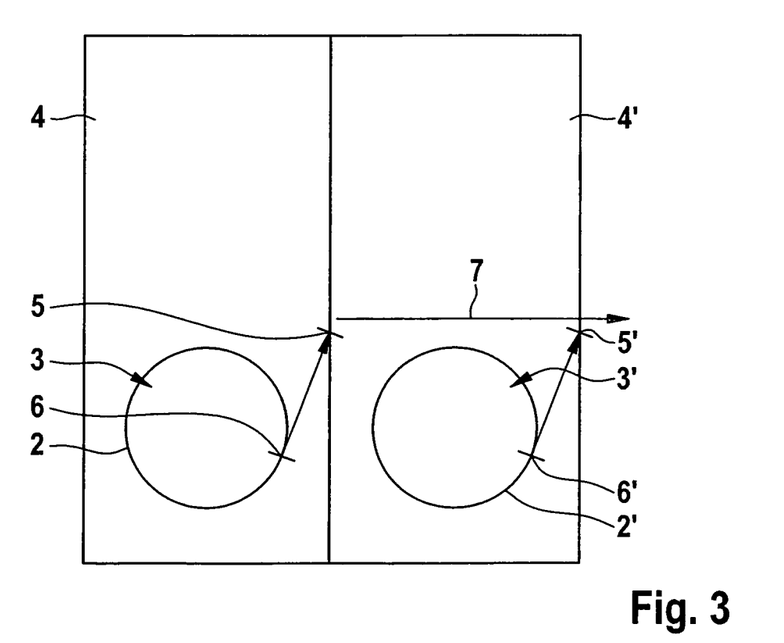
FIG. 3 shows a schematic top view of two paint or lacquer layers for illustrating specific embodiments of the movement of the friction element.

FIG. 3 is a schematic top view of two paint or lacquer layers 4, 4', and is used to illustrate possible friction element movements. FIG. 3 shows that for each paint or lacquer layer 4, 4', in each case a friction element (not illustrated) is initially moved in frictional contact along a circular path segment 2 into a test region 3, 3' of a paint or lacquer layer, and subsequently the frictional contact between the friction element and test region 3 is eliminated during movement of the friction element.

As indicated by reference numerals 5, 5', this may be carried out, for example, in that after running along circular path segment 2, 2' one or multiple times, during continuing movement the friction element is tangentially 5, 5' moved out of test region 3, 3' and lifted off outside test region 3, 3' of paint or lacquer layer 4, 4'.

However, as indicated by reference numerals 6, 6', it is also possible that after running along circular path segment 2, 2' one or multiple times, during continuing movement the friction element is lifted off test region 3, 3'.

After being lifted off paint or lacquer layer 4, 4', the test pieces may be moved away from paint or lacquer layer 4, 4' by translation in a direction 7 in order to be cleaned or disposed of, for example.

To achieve a rubout motion illustrated in FIG. 3, the testing device may include either one friction element moving device which is designed to move at least one first friction element and at least one second friction element in each case in frictional contact along a defined path 2, 2 over a test region 3, 3', or at least two friction element moving devices which are each designed to move at least one friction element in frictional contact along a defined path 2, 2' over a test region 3, 3'.

FIGS. 4a through 4d show schematic cross sections of first through fourth specific embodiments of a friction element moving device. The figures show that the friction element moving devices include a gripper 10, for example a vacuum gripper, for gripping, fixing, and releasing a friction element 1. This gripper 10 is mounted on a vertically movable shank 11 which is held vertically, via a guide 12, with respect to paint or lacquer layer 4 to be investigated.

Figure 4A:
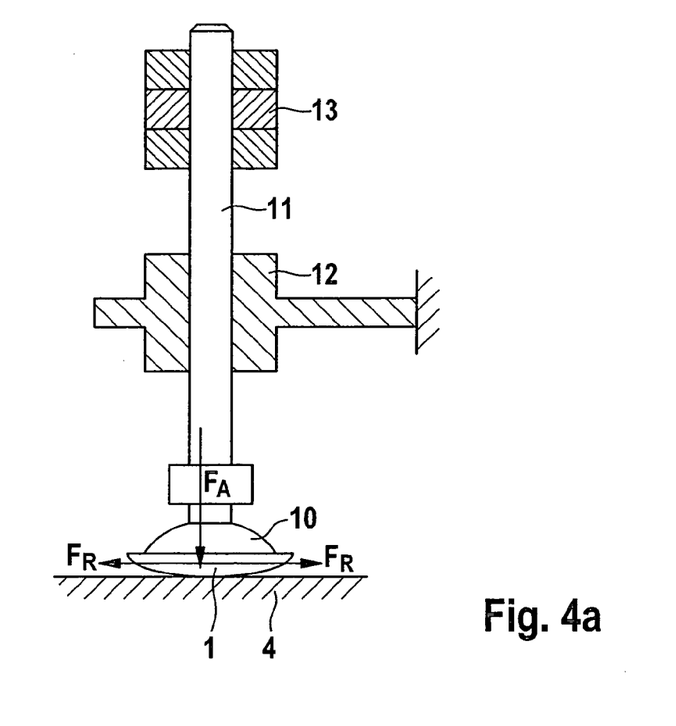
FIG. 4a shows a schematic cross section of a first specific embodiment of a friction element moving device.

In the specific embodiment shown in FIG. 4a, weights 13 may be attached to shank 11. A defined bearing force $F_A$ of friction element 1 on paint or lacquer layer 4 may be adjusted by attaching a defined number of weights 13. As an alternative to attaching a defined number of weights 13, the friction element moving device may include a weight-based bearing force adjusting device (not illustrated). The weight-based bearing force adjusting device may, for example, include a weight which is movably mounted in such a way that bearing force $F_A$ of friction element 1 on paint or lacquer layer 4 may be adjusted by changing the position of the movable weight. FIG. 4a also illustrates a force $F_R$ which acts laterally on friction element 1 during frictional contact, and which may be measured using a force sensor designed for this purpose.

Figure 4B:
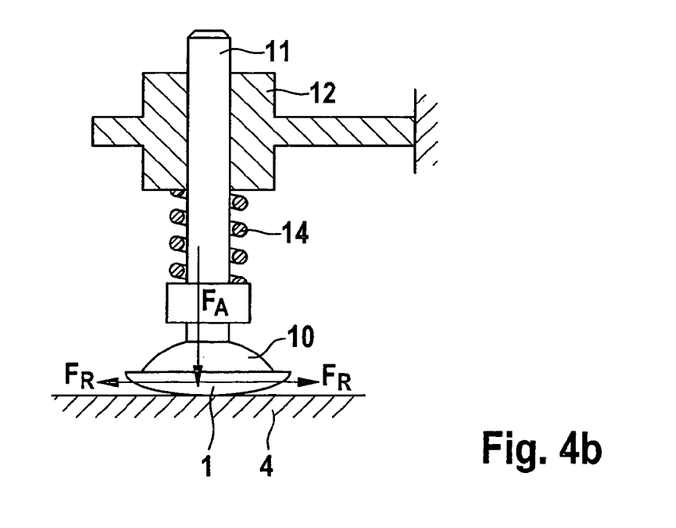
FIG. 4b shows a schematic cross section of a second specific embodiment of a friction element moving device.

The specific embodiment shown in FIG. 4b differs from the specific embodiment shown in FIG. 4a in that instead of weights 13 a spring 14 is situated between gripper 10 and guide 12 to ensure a defined bearing force $F_A$ of friction element 1 on paint or lacquer layer 4.

Figure 4C:
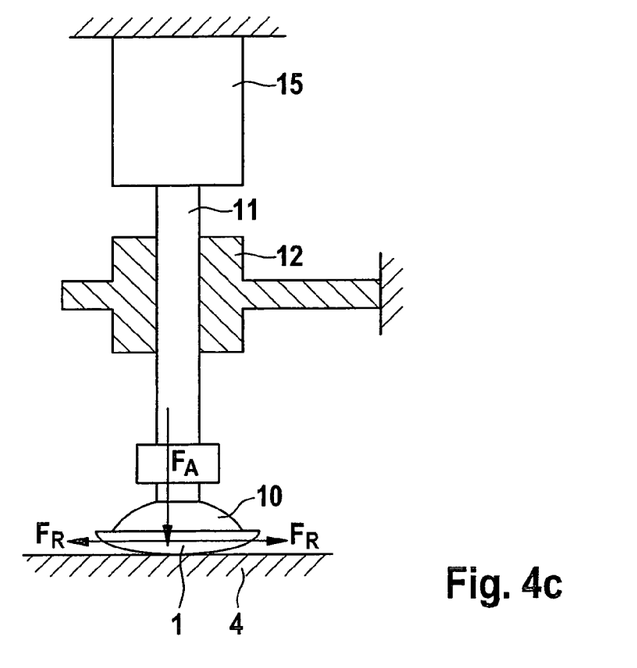
FIG. 4c shows a schematic cross section of a third specific embodiment of a friction element moving device.

The specific embodiment shown in FIG. 4c differs from the specific embodiment shown in FIG. 4a in that instead of weights 13 a pneumatic cylinder 15 is provided, with the aid of which bearing force $F_A$ of friction element 1 on paint or lacquer layer 4 may be automatically adjusted.

Figure 4D:
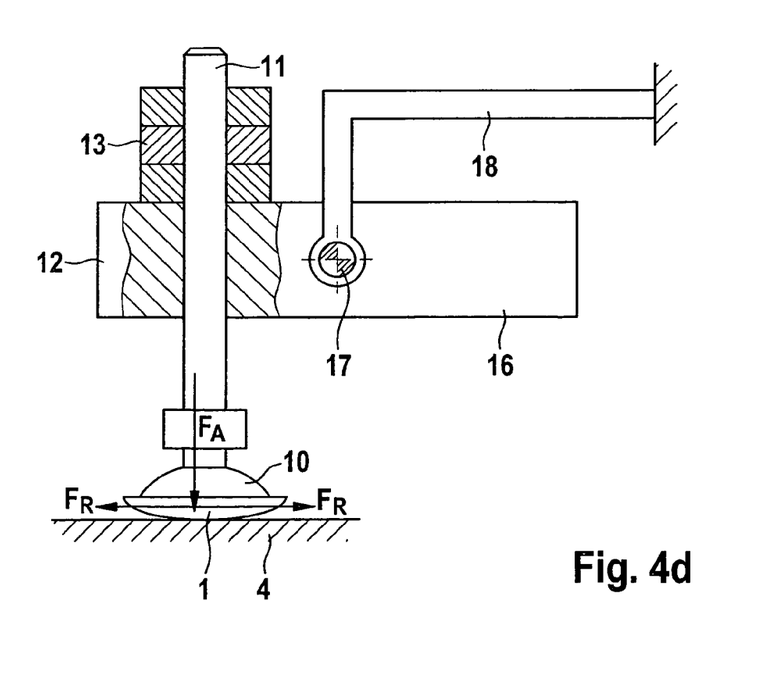
FIG. 4d shows a schematic cross section of a fourth specific embodiment of a friction element moving device.

The specific embodiment shown in FIG. 4d differs from the specific embodiment shown in FIG. 4a in that at the location of the vertically movable shank, friction element 1 is fixedly connected to a "weighing beam" 16 which is rotatably suspended at pivot point 17. In the present case, the friction element is adapted to the substrate not in the vertical direction, but, rather, on a circular path about pivot point 17. Bearing force $F_A$ of friction element 1 on paint or lacquer layer 4 may be adjusted corresponding to FIGS. 4a through 4c using weights, springs, or pneumatic cylinders.

Figure 5:
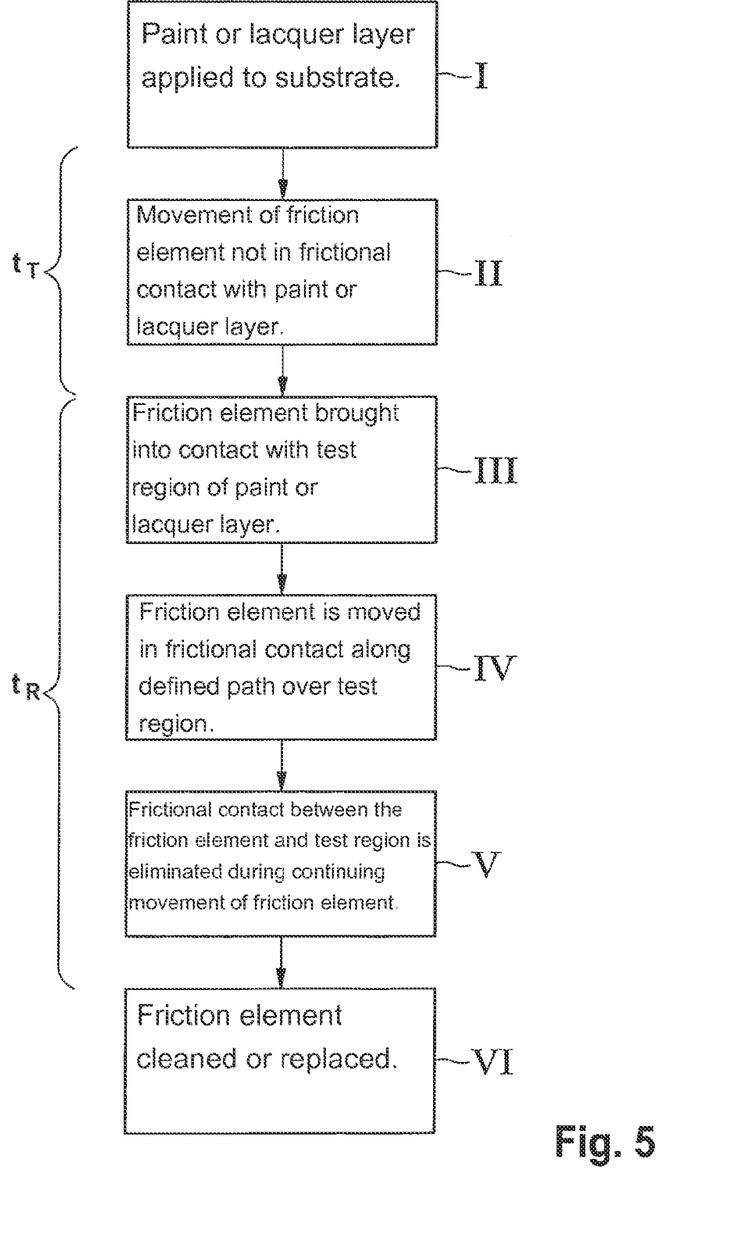
FIG. 5 shows a flow chart for illustrating one specific embodiment of the method according to the present invention.

FIG. 5 is a flow chart for illustrating one specific embodiment of the method according to the present invention. FIG. 5 illustrates that in a first method step I a paint or lacquer layer is automatically applied to a substrate, for example a test card, in particular using a blade coating, spray coating, roller coating, and/or spin coating method. The movement of a friction element with the aid of a friction element moving device is started in second method step II, at this point in time the friction element not yet being in frictional contact with a paint or lacquer layer. After a defined waiting time/drying time $t_T$ after applying the paint or lacquer layer in first method step I, in a third method step III the friction element during continuing movement is automatically brought into contact, in particular with a defined bearing force ($F_A$), with the test region of the paint or lacquer layer. The friction element is automatically moved in frictional contact along a defined path over the test region during a fourth method step IV. In a fifth method step V the frictional contact between the friction element and the test region is automatically eliminated during continuing movement of friction element 1, for example by moving the friction element out of the test region and/or by lifting the friction element from the test region. Force ($F_R$) which acts laterally on the friction element during the frictional contact is measured and used as a measure of the drying state of the paint or lacquer layer, and/or as a measure of the elimination of the frictional contact. FIG. 5 illustrates that, from the time that the friction element is placed on the paint or lacquer layer in method step III until the frictional contact is eliminated in method step V, the friction element is moved in frictional contact over the test region for a defined rubout time $t_R$. After fifth method step V, in a sixth method step VI the friction element may either be automatically cleaned or replaced with a new disposable friction element.

What is claimed is:

1. A testing device for checking the quality of one of a paint or lacquer layer, comprising:
    at least one friction element having a convex surface; and
    at least one friction element moving device configured to (i) initially move the at least one friction element in frictional contact along a defined path over a test region of the one of the paint or lacquer layer, and (ii) subsequently eliminate the frictional contact between the friction element and the test region during the movement of the friction element;
    wherein the friction element is adapted to frictionally contact the test region along the defined path after application of the one of the paint or lacquer layer and a defined waiting time;
    wherein the defined path is an at least partially curved path during the movement of the friction element; and
    wherein the defined path includes circular paths having different center points.

2. The testing device as recited in claim 1, wherein the friction element moving device is configured to at least one of move the friction element out of the test region and lift the friction element from the test region during movement of the friction element.

3. The testing device as recited in claim 1, wherein the friction element moving device is configured to provide at least one of the following: (i) the shape of the path is adjustable; (ii) a bearing force with which the friction element lies on the one of the paint or lacquer layer is adjustable; and (iii) a rubout time, defined as a time period during which the friction element is in frictional contact with the test region, is adjustable.

4. The testing device as recited in claim 1, wherein the friction element moving device includes at least one vacuum gripper configured to detachably fasten the friction element.

5. The testing device as recited in claim 1, wherein the friction element has a convex rubbing surface having the shape of one of a cambered disk, an ovaloid, or a semiovaloid.

6. The testing device as recited in claim 5, wherein the friction element is configured to be one of cleanable or disposable.

7. The testing device as recited in claim 1, wherein the friction element moving device is configured to place the friction element on the test region of the one of the paint or lacquer layer during movement of the friction element.

8. The testing device as recited in claim 1, wherein the friction element moving device includes at least one force sensor configured to measure a force which acts laterally on the friction element during the frictional contact.

9. The testing device as recited in claim 1, wherein at least two friction elements are provided, and wherein the friction element moving device is configured to move each of the two friction elements in frictional contact along a corresponding defined path over a corresponding test region.

10. The testing device as recited in claim 1, wherein at least two friction elements and at least two friction element moving devices are provided, and wherein each friction element moving device is configured to (i) move at least one friction element in frictional contact along a corresponding defined path over a corresponding test region of the one of the paint or lacquer layer, and (ii) eliminate the frictional contact between the friction element and the corresponding test region during the movement of the friction element.

11. The testing device as recited in claim 1, wherein the at least one friction element includes a flat surface situated opposite from the convex surface.

12. The testing device as recited in claim 1, wherein the defined path includes a first, curved path segment in the test region and a second, linear path segment outside the test region, such that the second path segment extends tangentially with respect to the first path segment.

13. The testing device as recited in claim 1, wherein the defined path includes a circular path rotation.

14. The testing device as recited in claim 13, wherein the convex surface of the friction element does not rotate around an inner axis of the friction element perpendicular to the test region.

15. An automated test method for checking the quality of one of a paint or lacquer layer, comprising:
    automatically moving at least one friction element in frictional contact along a defined path over a test region of the one of the paint or lacquer layer; and
    subsequently eliminating the frictional contact between the friction element and the test region during the movement of the friction element;
    wherein the friction element is brought into contact with the test region after a defined waiting time following application of the one of the paint or lacquer layer;
    wherein the defined path is an at least partially curved path during the movement of the friction element; and
    wherein the defined path includes circular paths having different center points.

16. The test method as recited in claim 15, wherein the frictional contact between the friction element and the test region is eliminated by at least one of: (i) moving the friction element out of the test region, and (ii) lifting the friction element from the test region during the movement of the friction element.

17. The test method as recited in claim 16, wherein:
    the one of the paint or lacquer layer is automatically applied to a substrate using at least one of a blade coating, spray coating, roller coating, and spin coating method;
    the friction element is automatically brought into contact, with a defined bearing force, with the test region after the defined waiting time following the application of the one of the paint or lacquer layer; and the friction element is moved in frictional contact over the test region for a predefined time period.

18. The test method as recited in claim 17, further comprising:

measuring a force which acts laterally on the friction element during frictional contact, wherein the measured lateral force is used as an indication of at least one of (i) the drying state of the one of the paint or lacquer layer, and (ii) the elimination of the frictional contact.

* * * * *